United States Patent

Seltzer et al.

[11] 4,150,234
[45] Apr. 17, 1979

[54] HYDANTOIN DIACRYLATE COMPOUNDS

[75] Inventors: Raymond Seltzer, New City; Joseph F. DiPrima, Hartsdale, both of N.Y.

[73] Assignee: Ciba-Geigy Corporation, Ardlsey, N.Y.

[21] Appl. No.: 711,001

[22] Filed: Aug. 2, 1976

[51] Int. Cl.² .......................................... C07D 233/72
[52] U.S. Cl. ............................... 548/312; 204/159.23; 526/258
[58] Field of Search .......................................... 548/312

[56] References Cited

U.S. PATENT DOCUMENTS

| 3,852,302 | 12/1974 | Habermeier et al. | 548/312 |
| 3,864,357 | 2/1975 | Porret et al. | 548/312 |

FOREIGN PATENT DOCUMENTS

| 978193 | 11/1975 | Canada | 548/312 |
| 2361493 | 6/1974 | Fed. Rep. of Germany | 548/312 |

Primary Examiner—Natalie Trousof
Attorney, Agent, or Firm—Vincent J. Cavalieri; Joseph F. DiPrima

[57] ABSTRACT

Hydantoin diacrylate compounds of the formula

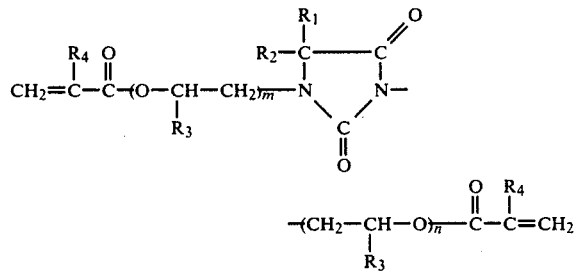

wherein $R_1$ is hydrogen, alkyl containing 1 to 8 carbon atoms; $R_2$ is alkyl containing 5 to 8 carbon atoms; each of $R_3$ and $R_4$ independently are hydrogen or methyl and m and n each represent an integer of from 1 to 30 are prepared. The diacrylate compounds are liquid at room temperature, easily processable as adhesives, casting and laminating resins and when cured possess excellent resistance to water.

7 Claims, No Drawings

HYDANTOIN DIACRYLATE COMPOUNDS

DETAILED DESCRIPTION

This invention relates to novel hydantoin diacrylate compounds of the formula

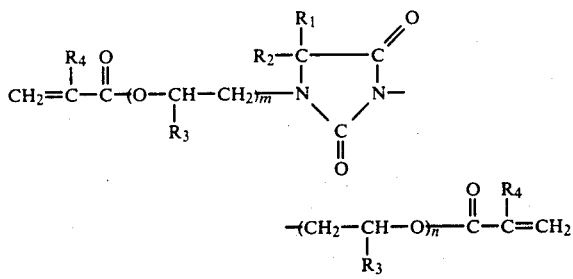

wherein $R_1$ is hydrogen, alkyl containing 1 to 8 carbon atoms, $R_2$ is alkyl containing 5 to 8 carbon atoms; and $R_3$ and $R_4$ independently are hydrogen or methyl; and m and n each represent an integer of from 1 to 30.

The alkyl group employed herein includes both straight- and branched-chain alkyl groups, examples of which are methyl, ethyl, propyl, isopropyl, butyl, isobutyl, pentyl, neopentyl, amyl, isoamyl, sec-amyl, hexyl, octyl and the like. One embodiment of this invention includes hydantoin diacrylate compounds of the above formula wherein each of m and n is 1.

Another embodiment of this invention includes hydantoin diacrylate compounds of the above formula wherein $R_1$ is H, or alkyl containing 1 to 6 carbon atoms; and each of m and n is 1 and $R_2$ is alkyl containing 5 to 6 carbon atoms.

Prior art hydantoin diacrylate compounds are disclosed in U.S. Pat. No. 3,852,302, which have the formula

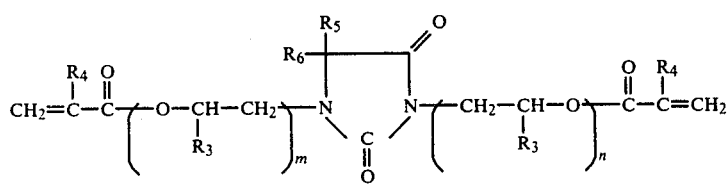

in which $R_5$ and $R_6$ each denote a hydrogen atom or a lower alkyl or alkenyl each having 1 to 4 carbon atoms, cycloalkyl or an optionally substituted phenyl, or in which $R_6$ and $R_5$ jointly form a tetramethylene or pentamethylene residue and m and n is an integer of from 1 to 30; $R_3$ and $R_4$ denote hydrogen or methyl.

The hydantoin diacrylate compounds of this patent however, have the disadvantage of displaying poor resistance to water. Thus, the mechanical and electrical properties for these cured products rapidly decay on exposure to water or humidity, rendering them of little value in these applications.

The diacrylate hydantoin compounds of this invention having an alkyl group of 5 to 8 carbon atoms in the 5 position of the hydantoin ring have the significant advantage over the "lower alkyl" examples described in the aforementioned patent, in that the cured compounds have greater water resistance. The compounds of this invention have good electrical properties and low viscosity which results in easy processing and are especially suitable as an adhesive, casting and laminating resin.

The diacrylates of this invention are simply prepared by adding 2 equivalents of acrylic or methacrylic acid to the hydantoin diols.

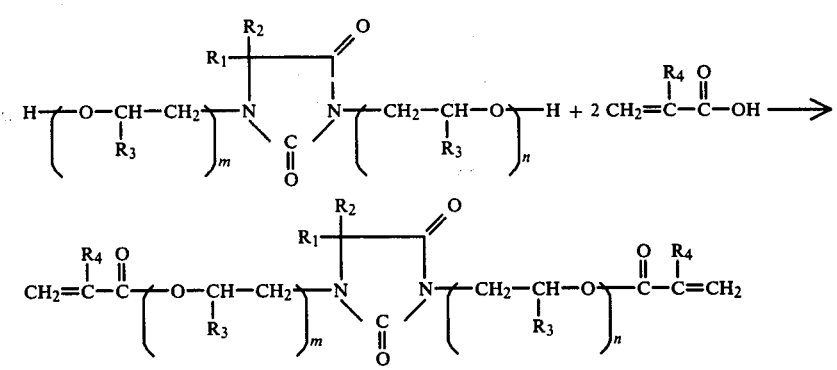

The intermediate hydantoins of the formula

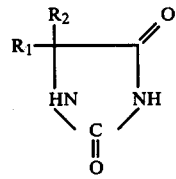

can be prepared by the well-known method of using a given ketone, sodium cyanide and ammonium carbonate. The hydantoin diols can then be prepared in the usual way using ethylene or propylene oxide and optionally a basic catalyst such as lithium chloride in a solvent such as dimethylformanide, e.g.,

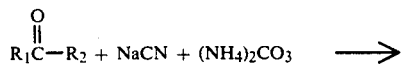

-continued

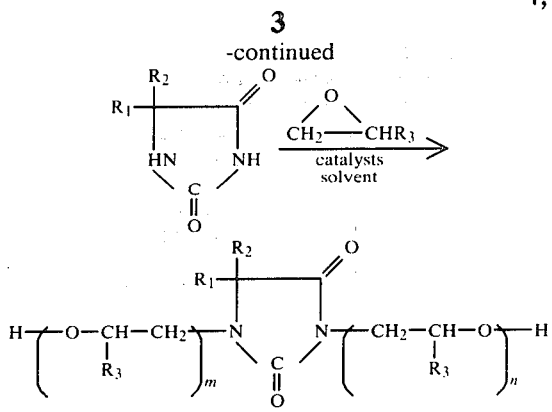

$R_1$, $R_2$ and $R_3$ in each of the above preparations are as hereinbefore defined.

The diacrylate hydantoin compounds of this invention are especially suitable for use as adhesives, casting and laminating resins and coatings. The curable diacrylates may be employed in the fields of adhesives, surface protection, the electrical industry, laminating processes and the building industry. More specifically, the diacrylate hydantoin compounds of this invention when combined with the appropriate curing agents or when photocured may be used as insulating compositions for electrical parts, as compositions to prepare printed circuit boards, can coatings, inks, as an adhesive and further, as compositions for the preparation of decorative laminates and flooring.

The diacrylate compounds according to the invention or their mixtures with other monomers and/or curing agents can be mixed, before curing, with customary modifiers, such as extenders, fillers and reinforcing agents, pigments, dyestuffs, plasticizers, flow control agents, agents for conferring thixotropy, flameproofing substances and mound release agents.

Suitable monomers which can be added to the diacrylate hydantoin compounds are, in particular, compounds of the acrylic acid series, such as esters from acrylic acid or methacrylic acid, and alcohols or phenols, e.g., methylacrylate, ethylacrylate, butylacrylate, dodecyacrylate, methymethacrylate, acrylonitrile, methacrylonitrile, ethylene glycol dimethacrylate, hexanediol diacrylate, pentairythritol triacrylate, trimethylolpropane triacrylate. It is moreover possible to use other reactive olefinic unsaturated monomers, such as, e.g., styrene, divinylbenzene, n-vinylpyrrolidone, vinyl esters such vinyl acetate, allyl compounds such as dialylphthalate, and others.

As extenders, reinforcing agents, fillers and pigments which can be introduced into the curable mixtures according to the invention there may, for example, be mentioned: coal tar, bitumen, glass fibers, boron fibers, carbon fibers, cellulose, polyethylene powder, slate powder, aluminum oxide trihydrate, chalk powder, gypsum, antimony trioxide, bentones, silica aerogel, (AEROSIL), lithopone, baryte, titanium dioxide, carbon black, graphite, iron oxide or metal powders, such as aluminum powder or iron powder.

The diacrylate hydantoin compounds according to this invention react with the customary free radical type curing agents or are curable with ionizing rays such as, gamma rays or electron beam radiation or by ultraviolet light in the presence of a photoinitiator.

The polyacrylate mixtures exhibit good adhesiveness on the surface of the base material and coatings can therefore be produced without difficulty on metals, wood, plastics, glass, paper, leather, etc.

The curing of the diacrylate compounds and mixtures can be carried out with any form of ionizing radiation, such as with a high-energy electromagnetic radiation such as, e.g., with Roetgen or gamma radiation, as well as with accelerated electrons. Using accelerated electrons, the process is performed with a mean electron energy of 50 KeV to 4,000 KeV. If it is required to cure thin layers, such as, e.g., coatings then a mean electron energy of 50 to 600 KeV and a curing dose of 0.5 to 5.0 Megarad, preferably of 1.0 to 3.0 Megarad, are applied.

Using ultraviolet radiation, it is necessary to have a photoinitiator present with the diacrylate hydantoin compounds and their mixtures. The photoiniator absorbs the radiation to produce free radicals which initiate polymerization. Examples of photoinitiators which may be used are as follows: (a) benzoin and benzoin ethers such as the methyl, ethyl and butyl derivatives, e.g., 2,2-diethoxyacetophenone, (b) benzophenone in combination with a catalyst such as triethylamine, N,N'-dimethylbenzylamine, dimethylaminoethanol, N-methyl-diethanolamine, and (c) benzophenone plus Michler's Ketone.

The photoinitiators are present in a concentration of from 0.05% to 10% and preferably 3% to 5% based on the weight of the diacrylate hydantoin compounds and their mixtures.

The diacrylates and their mixtures can be advantageously subjected, before, during or after curing, additionally to a heat treatment, which leads in some cases to a promotion of cross-linking.

Curing is advantageously performed in the absence of oxygen. In order to effect this, a protective gas atmosphere, e.g., nitrogen, is used.

It is advantageous in some cases to add to the diacrylate and/or its mixture small amounts of a polymerization catalyst forming free radicals, such as, e.g., peroxides, azo compounds, or persulphates.

The customary catalysts which form free radicals may be used for the polymerization or copolymerization; there may be mentioned hydrazine derivatives, for example hydrozine hydrochloride, organometallic compounds, such as lead tetraethyl and, in particular, aliphatic azo compounds, such as $\alpha$, $\alpha'$-azoisobutyroinitrile and organic peroxides or persalts, such as, for example, peracetic acid, acetyl peroxide, chloroacetyl peroxide, trichloroacetyl peroxide, benzoyl peroxide, chlorobenzoyl peroxide, benzoyl acetyl peroxide, propionyl peroxide, fluorochloropropionyl peroxide, luryl peroxide, cumene hydroperoxide, cyclohexanone hydroperoxide, tert.-butyl hydroperoxide, di-tert.-butyl peroxide, di-tert.-amyl peroxide and p-methane hydroperoxide, and also inorganic peroxide compounds, such as sodium peroxide, alkali percarbonates, alkali persulphates or alkali perborates, and especially hydrogen peroxide, which can advantageously replace the more expensive benzoyl peroxide. The amount added is chosen, in a known manner, in accordance with the desired course of the reaction or in accordance with the desired properties of the polymer; advantageously, about 0.05 to 10 percent by weight of the catalyst, calculated relative to the total weight of the diacrylate or diacrylatemonomer mixture, are employed, with the total amount of the catalyst being added either initially or in portions during the course of the polymerization.

In certain cases, cationic or anionic catalysts can also be used.

To further illustrate the nature of this invention and the processes employed in preparing and curing the diacrylate hydantoin resins of this invention, the following examples are given below:

A. Preparation of Hydantoins

5-sec-Amyl-5-Ethylhydantoin

To a slurry of ammonium carbonate (865 parts), sodium cyanide (180 parts) in water (1200 parts) was added 5-methyl-3-heptanone (385 parts) in ethanol (1200 parts) at ambient temperature with stirring. The reaction mixture was heated to 55° C. over a period of 30 minutes and maintained at 55° C. for 6 hours. After cooling to ambient temperature, chloroform (1000 parts) was added and the mixture stirred for ten minutes. The reaction mixture was filtered and the filter cake washed with additional chloroform (500 parts). The organic phase was collected and the aqueous phase washed with additional chloroform (1000 parts) in two portions. The combined organic phase was evaporated to dryness yielding crude product. The resultant white solid was slurried in water (2000 parts), filtered and dried to constant weight to afford 5-sec-amyl-5-ethylhydantoin (560 parts, 94% yield, mp 151–156° C.).

Cal'c: C, 60.58; H, 9.15; N, 14.13.
Found: C, 60.54; H, 9.44; N, 14.04.

The following hydantoin were prepared employing the above procedure:
5-n-Amyl-5-methylhydantoin (Mp 101–103°C., 94%)
5-i-Amyl-5-methylhydantoin (Mp 158–161° C., 90%)
5-n-Hexyl-5-methylhydantoin (Mp 107–110°, 96%)

In a similar manner, by substituting the appropriate ketone or aldehyde for the 5-methyl-3-heptanone in the above example, the following hydantoin compounds are obtained:
5-amylhydantoin
5-hexyl-5-ethylhydantoin
5-octylhydantoin
5-heptyl-5-methylhydantoin
5-octyl-5-amylhydantoin
5,5-dioctylhydantoin

B. Preparation of Hydantoin Diols

Preparation of 1,3-Bis-(2'-Hydroxyethyl)-5-sec-amyl-5-ethylhydantoin

Into ta two-liter round bottom flask, equipped with stirrer, thermometer, and dry ice-acetone condenser, was added 198.2 g. of 5-sec-amyl-5-ethylhydantoin (1.0 mole), 4.25 g. of lithium chloride, and 300 g. of dimethylformamide at ambient temperature. To the reaction mixture was also added a solution of 132 g. of ethylene oxide (3.0 moles) in 400 g. of dimethylformamide and the mixture heated slowly to 90° C. After 4 hours at 90° C. the reaction mixture was cooled to 30° C. and filtered. The solvent was then removed at reduced pressure and the product was distilled from the crude residue to affort a pale yellow liquid in 84% yield. The proton-magnetic resonance spectrum is in agreement with the proposed structure.

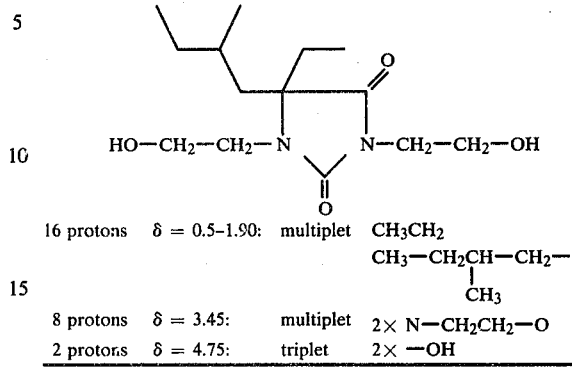

| | | | |
|---|---|---|---|
| 16 protons | δ = 0.5–1.90: | multiplet | CH$_3$CH$_2$ CH$_3$—CH$_2$CH—CH$_2$— | CH$_3$ |
| 8 protons | δ = 3.45: | multiplet | 2× N—CH$_2$CH$_2$—O |
| 2 protons | δ = 4.75: | triplet | 2× —OH |

In a similar manner, by substituting the appropriate hydantoin for the 5-sec-amyl-5-ethylhydantoin in the above example, the following dials compounds are obtained:

1,3-bis-(2'-hydroxyethyl)-5-n-amyl-5-methylhydantoin
1,3,bis-(2'-hydroxyethyl)-5-i-amyl-5-methylhydantoin
1,3-bis-(2'-hydroxyethyl)-5-n-hexyl-5-methylhydantoin
1,3-bis-(2'-hydroxyethyl)-5-amylhydantoin
1,3-bis-(2'-hydroxyethyl)-5-hexyl-5-ethylhydantoin
1,3-bis-(2'-hydroxyethyl)-5-octylhydantoin
1,3-bis-(2'-hydroxyethyl)-5-heptyl-5-methylhydantoin
1,3-bis-(2'-hydroxyethyl)-5-octyl-5-amylhydantoin
1,3-bis-(2'-hydroxyethyl)-5,5-di-n-octylhydantoin

C. Preparation of Diacrylates

Preparation of 1,3-Bis-(2'-acryloxyethyl)5-sec-amyl-5-ethylhydantoin

Into a one-liter round bottom flask, equipped with stirrer, thermometer, condenser, and Dean Stark trap was added 50 g. of 1,3-Bis-(2'-hydroxyethyl) 5-sec-amyl-5-ethylhydantoin (0.175 moles) as prepared in the previous Example 37.8 g. of acrylic acid (0.525 mole), 5.0 g of paratoluenesulfonic acid, 0.1 g. of hydroquinone and 250 ml of toluene. The reaction mixture was heated to reflux and water formed during the reaction was azeotropically removed. After 6.3 ml of water (93% of theory) was collected in the trap, the reaction mixture was cooled to 10° C. and filtered. The toluene solution was first washed with 150 ml of water, and then with a 5% aqueous ammonia solution containing 10% ammonium chloride followed by a third wash with 200 ml. of water. The toluene solution was then dried over anhydrous sodium sulfate and evaporated to dryness to afford a pale brown, clear, low viscosity resin in 87% yield with acrylate value of 4.19 equiv/kg. (83% theory). The proton-magnetic spectrum is in agreement with the proposed structure.

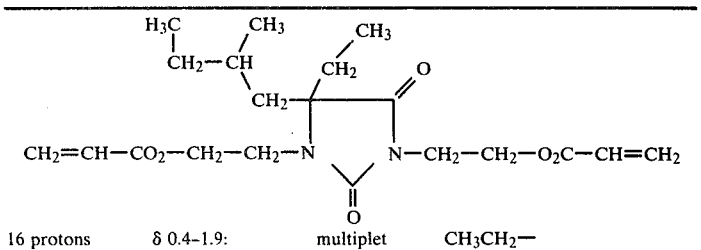

| | | | |
|---|---|---|---|
| 16 protons | δ 0.4–1.9: | multiplet | CH$_3$CH$_2$— |

| | | | |
|---|---|---|---|
| | | | CH₃CH₂—CH—CH₂—<br>       \|<br>       CH₃ |
| 8 protons | 3.4–3.8: | multiplet | 2× N—CH₂CH₂—O |
| 6 protons | 5.8–6.4: | multiplet | $$2\times\ CH_2{=}CH{-}\overset{\displaystyle O}{\underset{\|}{C}}{-}$$ |

In a similar manner, by substituting the following hydantoin diols for the 1,3-bis-(2-hydroxyethyl)-5-sec-amyl-5-ethylhydantoin in the above example.

1,3-bis-(2'-hydroxyethyl)-5-n-amyl-5-methylhydantoin
1,3-bis-(2'-hydroxyethyl)-5-i-amyl-5-methylhydantoin
1,3-bis-(2'-hydroxyethyl)-5-n-hexyl-5-methylhydantoin
1,3-bis-(2'-hydroxyethyl)-5-amylhydantoin
1,3-bis-(2'-hydroxyethyl)-5-hexyl-5-ethylhydantoin
1,3-bis-(2'-hydroxyethyl)-5-octylhydantoin
1,3-bis-(2'-hydroxyethyl)-5-heptyl-5-methylhydantoin
1,3-bis-(2'-hydroxyethyl)-5-octyl-5-amylhydantoin
1,3-bis-(2'-hydroxyethyl)-5,5-di-n-octylhydantoin there are obtained the following diacrylate hydantoin compounds:

1,3-bis-(2'-acryloxyethyl)-5-n-amyl-5-methylhydantoin
1,3-bis-(2'-acryloxyethyl)-5-i-amyl-5-methylhydantoin
1,3-bis-(2'-acryloxyethyl)-5-n-hexyl-5-methylhydantoin
1,3-bis-(2'-acryloxyethyl)-5-amylhydantoin
1,3-bis-(2'-acryloxyethyl)-5-hexyl-5-ethylhydantoin
1,3-bis-(2-acryloxyethyl)-5-octylhydantoin
1,3-bis-(2'-acryloxyethyl)-5-heptyl-5-methylhydantoin
1,3-bis-(2'-acryloxyethyl)-5-octyl-5-amylhydantoin
1,3-bis-(2'-acryloxyethyl)-5,5-n-octylhydantoin respectively.

Preparation of 1,3-Bis-(2'-Methacryloxyethyl-5-sec-amyl-5-ethyl-hydantoin 50 g. of 1,3-Bis-(2'-hydroxyethyl)-5-sec-amyl-5-ethylhydantoin (0.175 mole), reacts with 45.2 g of methacrylic acid (0.525 mole) at reflux analogously to the previous example to afford the desired product.

Curing Experiments

Ultraviolet light induced polymerization of the hydantoin diacrylates 100 parts of 1,3-bis-(2'-acryloxyethyl)-5-sec-amyl-5-ethylhydantoin was mixed with 2.5 parts benzophenone and 2.5 parts of dimethylethanolamine to aford a low viscosity light brown solution. A film of this solution of aluminum was irradiated 10 seconds by a 200 watt/in medium pressure mercury vapor lamp at a distance of 3 inches to afford a hard, tack-free, solvent resistant film.

A film from a solution of 80 parts of 1,3-bis-(2'-acryloxyethyl)-5-sec-amyl-5-ethylhydantoin, 20 parts of N-vinyl-pyrrolidone, 2.5 parts of benzophenone and 2.5 parts of dimethylethanolamine was drawn an aluminum. irradiation as describen in the above example, gave a tack-free, hard, solvent resistant film.

Peroxide induced polymerization of higher alkyl hydantoin diacrylates 100 parts of 1,3-bis-(2'-acryloxyethyl)-5-sec-amyl-5-ethylhydantoin is stirred at 70° C. with 1.5 parts of 50% strength cyclohexanone hydroperoxide, and then polymerized over the course of 2 hours/80° C. and 12 hours/120° C. in an aluminum mold to afford a tough, solvent resistant plaque.

What is claimed is:

1. An hydantoin diacrylate compound of the formula

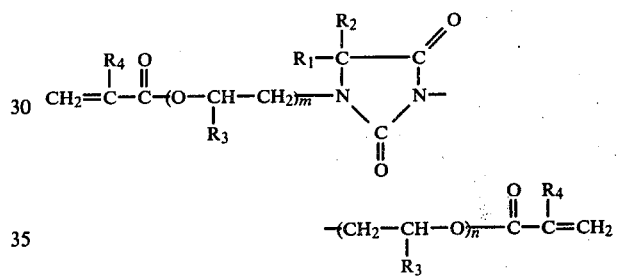

wherein $R_1$ is hydrogen, alkyl containing 1 to 8 carbon atoms; $R_2$ is alkyl containing 5 to 8 carbon atoms; each of $R_3$ and $R_4$ independently are hydrogen or methyl; and m and n each represent an integer of from 1 to 30.

2. The hydantoin diacrylate of claim 1 wherein each of m and n is 1.

3. The hydantoin diacrylate of claim 1 wherein $R_1$ is hydrogen or alkyl containing 1 to 6 carbon atoms; $R_2$ is alkyl containing 5 to 6 carbon atoms; and each of m and n is 1.

4. The hydantoin diacrylate of claim 1 wherein $R_1$ is methyl; $R_2$ is n-amyl; each of $R_3$ and $R_4$ is hydrogen; and each of m and n is 1.

5. The hydantoin diacrylate of claim 1 wherein $R_1$ is ethyl; $R_2$ is sec-amyl; each of $R_3$ and $R_4$ is hydrogen; and each m and n is 1.

6. The hydantoin diacrylate of claim 1 wherein $R_1$ is ethyl; $R_2$ is sec-amyl; $R_3$ is hydrogen; $R_4$ is methyl; and each of m and n is 1.

7. The hydantoin diacrylate of claim 1 wherein $R_1$ is methyl; $R_2$ is n-hexyl; each of $R_3$ and $R_4$ is hydrogen; and each of m and n is 1.

* * * * *